(12) United States Patent
Lee

(10) Patent No.: US 10,131,867 B2
(45) Date of Patent: Nov. 20, 2018

(54) DEVICE FOR PUTTING MATERIAL INTO CELL

(71) Applicant: FEMTOBIOMED INC., Seongnam-si, Gyeonggi-do (KR)

(72) Inventor: Sanghyun Lee, Pohang-si (KR)

(73) Assignee: FEMTOBIOMED INC., Seongnam-si (KR)

( * ) Notice: Subject to any disclaimer, the term of this patent is extended or adjusted under 35 U.S.C. 154(b) by 206 days.

(21) Appl. No.: 14/980,682

(22) Filed: Dec. 28, 2015

(65) Prior Publication Data

US 2016/0186118 A1 Jun. 30, 2016

(30) Foreign Application Priority Data

Dec. 28, 2014 (KR) .......................... 10-2014-0191302
Dec. 14, 2015 (KR) .......................... 10-2015-0178130

(51) Int. Cl.
| | |
|---|---|
| *C12M 1/42* | (2006.01) |
| *C12M 3/06* | (2006.01) |
| *C12M 1/00* | (2006.01) |
| *C12N 15/87* | (2006.01) |

(52) U.S. Cl.
CPC ............ *C12M 35/02* (2013.01); *C12M 23/16* (2013.01); *C12M 23/22* (2013.01); *C12M 35/04* (2013.01); *C12N 15/87* (2013.01)

(58) Field of Classification Search
CPC ...... C12M 23/16; C12M 23/22; C12M 35/02; C12M 35/04; C12N 15/87
See application file for complete search history.

(56) References Cited

U.S. PATENT DOCUMENTS

| | | |
|---|---|---|
| 6,380,183 B1 | 4/2002 | Schreiner et al. |
| 6,998,245 B1 | 2/2006 | Uemura et al. |
| 7,338,796 B1 * | 3/2008 | Davalos ............... B01F 5/0475 |
| | | 422/81 |
| 2003/0148334 A1 | 8/2003 | Sun et al. |

(Continued)

FOREIGN PATENT DOCUMENTS

| | | |
|---|---|---|
| JP | 2002-516678 A | 6/2002 |
| JP | 2004-248653 | 9/2004 |

(Continued)

OTHER PUBLICATIONS

Boukany et al., "Nanochannel electroporation delivers precise amounts of biomolecules into living cells," Nature Nanotechnology, 6: 747-754, Nov. 2011.
Choudhury et al., "Continuous flow single cell electroporation in an ultrafast laser inscribed optofluidic device," International Conference on Fiber Optics and Photonics, 3 pages, 2012.
Gao et al., "Design of a Microchannel-Nanochannel-Microchannel Array Based Nanoelectroporation System for Precise Gene Transfection," Small, 10(5): 1015-1023, Mar. 12, 2014.

(Continued)

*Primary Examiner* — William H. Beisner
(74) *Attorney, Agent, or Firm* — Lewis Roca Rothgerber Christie LLP

(57) ABSTRACT

The present invention relates to a device for putting material into a cell to be modified. More particularly, the present invention is directed to a device formed within one solid material and comprises, a first passage on which the cell passes; a second passage on which the material passes and connected to the first passage at a position randomly selected between both ends of the first passage; and an apparatus which applies pressure difference or electric potential difference on the first passage and the second passage, and is also directed to a process for making the device.

12 Claims, 7 Drawing Sheets

(56) References Cited

U.S. PATENT DOCUMENTS

| | | |
|---|---|---|
| 2008/0248575 A1 | 10/2008 | Lee et al. |
| 2012/0004144 A1 | 1/2012 | Perroud et al. |
| 2013/0122592 A1 | 5/2013 | Hayakawa et al. |
| 2014/0256047 A1 | 9/2014 | Lee et al. |

FOREIGN PATENT DOCUMENTS

| | | |
|---|---|---|
| JP | 2005-510236 A | 4/2005 |
| KR | 10-2016-0079660 | 7/2016 |
| WO | WO 89/03426 | 4/1989 |
| WO | WO 2004/092369 A1 | 10/2004 |
| WO | WO 2005/056788 A1 | 6/2005 |
| WO | WO 2012/158631 A2 | 11/2012 |
| WO | WO 2013/059343 A1 | 4/2013 |
| WO | WO 2014/096055 A1 | 6/2014 |

OTHER PUBLICATIONS

Geng et al., "Transfection of cells using flow-through electroporation based on constant voltage," Nature Protocols, 6(8): 1192-1208, 2011.

Sharei et al., "A vector-free microfluidic platform for intracellular delivery," PNAS, 110(6): 2082-2087, Feb. 5, 2013.

Zhu et al., "Electroporation based on hydrodynamic focusing of microfluidics with low dc voltage," Biomed Microdevices, 12:35-40, 2010.

Lee, "Femtosecond Laser Nanomachining and Applications to Micro/Nanofluidics for Single Cell Analysis," 124 pages, 2008.

Stewart et al., "In vitro and ex vivo strategies for intracellular delivery," Nature, 538:183-192, Oct. 2016.

Sun et al., "Single-cell microfluidic impedance cytometry: a review," Microfluid Nanofluid, 8:423-443, 2010.

\* cited by examiner

DEVICE FOR PUTTING MATERIAL INTO CELL

CROSS-REFERENCE TO RELATED APPLICATIONS

This applications claims priority to Korean Patent Application Nos. 10-2014-0191302, filed Dec. 28, 2014 and 10-2015-0178130, filed Dec. 14, 2015, the disclosures of which are incorporated herein by reference.

TECHNICAL FIELD

The present invention relates to a device for putting material into a cell to be modified. More particularly, the present invention is directed to a device formed within one solid material and comprises, a first passage on which the cell passes; a second passage on which the material passes and connected to the first passage at a position randomly selected between both ends of the first passage; and an apparatus which applies pressure difference or electric potential difference on the first passage and the second passage, and is also directed to a process for making the device.

BACKGROUND OF THE INVENTION

Recently, various researches for new biomedical technology have been actively progressed by means of the fusion of biotechnology, electronic technology and nano-technology which have been also remarkably developed lately.

Numerous attempts have been made to use patient's cells manipulated in vitro for medical treatment. Various R&D projects for developing new drug for next generation and verifying the drug target by manipulating human cell have been progressed.

The cell manipulation technologies have focused on the development of useful cellular therapeutics. Particularly, various exertions for cell therapy which utilizes the IPS (Induced Pluripotent Stem) cells induced by Yamanaka factor have been tried.

Yamanaka factors refer to four genes, Oct3/4, Sox2, cMyc and K1f4. The insertion of the four genes into the chromosome of a cell by using the vector originated from virus, can transform the somatic cell which already finished differentiation into pluripotent stem cell which can differentiate into various somatic cells. The IPS cell has been evaluated as an innovative technology which can overcome the ethics problem and productivity problem of the embryonic stem cell, and can also obviate the limitations in differentiation capability of the adult stem cell.

However, the IPS cell cause a safety problem that the vector derived from the virus inserted into a live-cell together with the Yamanaka factors. Also, in case of transplantation of the cell or tissue differentiated from the IPS cells which contains the vector derived from the virus into the human body, there may be another problem that tumor risk is increased.

Therefore, new technologies for injecting various materials, such as, DNA, RNA, polypeptide, or nano-particle, directly into a cell without using delivery vehicle, have been required in order to develop new cellular therapeutics which can avoid the above risk caused by using of the viral vector.

In the conventional cell manipulation technologies which do not employ any delivery vehicle, the typical process is to damage the membrane of the cells by mechanical shear force, chemical treatment or by applying electric field and then to allow the material such as genes which exist in extra-cellular fluids to flow into the cell through the damaged membrane gaps, and to expect the damaged cell membrane to be recovered by self-healing capacity of the cell.

A variety of cell transfection techniques, such as particle bombardment, micro-injection and electroporation, have been developed. Except for the micro-injection, these techniques are based on bulk stochastic processes in which cells are transfected randomly by a large number of genes or polypeptides.

The disadvantage of the conventional bulk electroporation the most widely used process for transfection of cells is that the injected dose cannot be controlled.

Therefore, microfluidics-based electroporation has emerged as a new technology for individual cell transfection. The microfluidics-based electroporation offers several important advantages over the bulk electroporation, including lower poration voltages, better transfection efficiency and a sharp reduction in cell mortality.

In 2011, a nanochannel electroporation technology which expose a small area of a cell membrane positioned adjacent to a nanochannel to very large local electric field strength, was disclosed to the public (L. James Lee et al, "Nanochannel electroporation delivers precise amounts of biomolecules into living cells", Nature Nanotechnology Vol. 6, November 2011, www.nature.com/naturenanotechnology published online on Oct. 16, 2011).

The nanochannel electroporation device comprises two micro channels connected by a nanochannel. The cell to be transfected is positioned in one microchannel to lie against the nanochannel, and other microchannel is filled with the agent to be delivered. The microchannel-nanochannel-microchannel design enables the precise placement of individual cells. One or more voltage pulses lasting milliseconds is delivered between the two microchannels, causing transfection. Dose control is achieved by adjusting the duration and number of pulses.

By the way, the nanochannel electroporation device disclosed in the above prior art employs PDMS (polydimethylsiloxane) lid that covers microchannel and nanochannels made by polymeric resin through imprinting and formed over the chip substrate.

Therefore, the nanochannel electroporation chip described in the article of Nature Nanotechnology, cannot avoid the chinks occurred between the polydimethylsiloxane lid and the imprinted layer of microchannels and nanochannels made by polymeric resin, because the sealing between the lid and the channel layer of which mechanical properties is different from each other, cannot be absolutely perfect.

Also, since the size stabilities of the polydimethysiloxane lid and the microchannels and nanochannels made by polymeric resin, are low, the sealing between the lid and the layer of channels cannot be perfect. Therefore, the chinks may easily occur between the lid and the layer of channels. The chinks allows the infiltration of the solution which causes the contamination of nanochannel electroporation chip and also generate various aberration of electric field and pressure difference applied for the transfer of cell between the channels and for injection of the transfection agent into the cell.

Therefore, new technology which can put various materials quantitatively into individual cell and can control the amount of the material without such contamination or aberration caused by the contamination has long been anticipated in this technology field.

The inventor of the present application conceived the device for putting material into a cell without using delivery vehicle, formed within one solid material without any sealing in order to exclude the possibility of the occurrence of the chink intrinsically, and thereby, can obviate disadvantages of the prior art, such as the contamination and aberration caused by the chink.

Therefore, the primary object of the present invention is to provide a device for putting material into a cell, formed within one solid and comprises: a first passage on which the cell passes; a second passage on which the material passes and connected to the first passage at a position randomly selected between both ends of the first passage; and an apparatus which applies pressure difference or electric potential difference on the first passage and the second passage.

Another object of the present invention is to provide a process for forming a device for putting material into a cell within one solid by irradiation of LASER, which comprises the steps of: (i) forming a first passage on which the cell passes within the one solid by irradiation of LASER; (ii) forming a second passage on which the material passes and connected the second passage to the first passage at a position randomly selected between both ends of the first passage within the one solid by irradiation of LASER; and (iii) installing an apparatus which applies pressure difference or electric potential difference on the first passage and the second passage.

DISCLOSURE OF INVENTION

The primary object of the present invention can be achieved by providing a device for putting material into a cell, formed within one solid and comprises a first passage on which the cell passes; a second passage on which the material passes and connected to the first passage at a position randomly selected between both ends of the first passage; and an apparatus which applies pressure difference or electric potential difference on the first passage and the second passage.

LASER means Light Amplification Stimulated Emission of Radiation and may be classified into either pulsed or continuous beams. The femto-laser is one of the pulsed beam lasers. The major parameters of pulsed beam lasers are repetition rate, wavelength, pulse energy, and pulse width. Among them, the pulse width has well characterized pulsed beam lasers such as nanosecond (ns, $10^{-9}$) lasers, pico second (ps, $10^{-12}$) lasers, and femto second (fs, $10^{-15}$) lasers. As such, femto-lasers indicate pulsed beam lasers having the pulse width of 1-999 femto second.

Femto second, which is one millionth of nanosecond, is indeed blazingly short period of time. The time scales of phenomena in nature are much slower than femto seconds. So scientists could have made the fastest phenomena in nature easily analyzed by freezing in time. The first femto-laser had been invented to visualize the electron reaction in chemistry. Not only the femto-laser pules are ultrafast, but the light-matter reaction in femto second regime becomes significantly different due to the multi-photon phenomena.

The special features of femto-laser beams have enabled many previously impossible processes. One is the heat-free ablation. Femto-laser doesn't rely on the heat to ablate matters, but it stripes away the valence electrons to ionize materials. So, the materials can be cut without the heat affected damages nearby.

And it was found that the multi-photon ionization by femto-laser pulses is extremely deterministic and can be localized in nanometer scale, overcoming the diffraction limit of resolution in light interaction. In femto second regime, it was proved that even visible light can achieve the nanometer scale ablation of matters.

In addition, femto-laser pulses can also ablate transparent materials such as glass. So it can be applied to diverse applications in medical devices. Considering that the difficulties of providing affordable hard X-ray light sources, femto-laser-based 3D nano-machining can greatly contribute in the nanoscience and nanoengineering especially for biomedical applications.

The micro channels and nano channels of the device of the present invention, on which the fluid containing cell flow, may be formed within one solid material, such as glass, by irradiation of the femto-laser on the one solid material.

Microfluidics which had emerged in 2000 mainly deals with the analysis and manipulation of biomedical samples based on the micro-scale fluidic channel networks. The microfluidic chips have complex fluidic networks, where diverse biochemical surface treatments are engineered; electrochemical manipulations are performed; and pressure-driven or electro osmotic flow is driven to circulate the chip.

Thus, there are a lot of standards which the microfluidic chip should meet for the medical applications. And many of them can be ideally met with the incorporation of glass as the material of the microfluidic chip. This is because the glass has long been used and approved in the medical fields. Specifically, glass can well satisfy the biological compatibility, chemical resistance, electrical insulation, dimensional stability, structural strength, hydrophilicity, and transparency.

Nevertheless, incorporating glass as the material of microfluidic chips has difficulties and limitations originated from the etch-bond process such that the isotropic glass etching limits resolution, aspect ratio, and cross-sectional shape of the channels. In addition, the glass to glass bonding to complete the microfluidic chip fabrication is not only difficult and expensive, but it also radically limits to build true three-dimensional structures especially in nanoscales. Instead, PDMS silicon molding processes had wide spread owing to the fact that it is cheap, easy to replicate many times, and weak but simple bonding process to glass.

While the PDMS molding is great alternative for research purposes, it is still limited to be used for the medical purposes due to the low bio-compatibility, bad chemical resistance, dimensional instability, structural weakness, and incomplete bonding. The incomplete bonding can easily allow the current and fluid to leak along the bonding interfaces. Considering that improving the performance of the microfluidic operation is dependent upon increasing the press or the electric fields, PDMS molding would be incompatible to the medical grade microfluidic operation in many cases.

When cells are manipulated in microfluidic chips, the pressure and the electric potentials should not be limited to maximize the performance and the operational freedom due to the structural weakness and the incomplete bonding issue. The structural strength can be overcome by adopting rigid and stable solids as the base material with acceptable transparency such as glass, polymethylmethacrylate (PMMA), polycarbonate (PC), and so on. However, it is still required to significantly improve the glass-etch-bond process to take the huge advantages of glass in the microfluidic medical applications.

In the current glass-etch-bond processes, the lid glass on which microfluidic channel networks are etched is bonded to the flat bottom one by applying heat or plasma in dust-free conditions. This process is great for mass-producing two-dimensional microscale fluidic chips. However, realizing true tree-dimensional nanoscale structures by the glass-etch-bond process is significantly limited by the isotropic etching and the requirement for the glass-to-glass direct bonding.

The laser processing is thus promising, where the bonding process can be removed. Furthermore, research in the Univ. of Michigan, USA found that true three-dimensional nano-machining of glass is possible by incorporating the femto-second laser pulses in 2004. Afterwards, femtosecond nano-machining has been developed, realizing the direct processing of true three-dimensional nanoscale structures in a single glass plate without bonding.

In most cases, it is much more convenient and efficient to prepare microscale two-dimensional channels based on the conventional etch-bond process and to process the rest of the nanoscale and three-dimensional structures by the femto-laser nanomachining. It is because the material removal of femto-laser nanomachining is inevitably very slow and localized, whereas the etching process can be effective for the large area processing.

The device of the present invention is formed within one solid material, such as, glass, thermoplastic polymers or thermosetting polymers, for example, polycarbonate, acrylics, epoxy resin or polyimide. The solid material is desirably selected from glass, thermoplastic polymers or thermosetting polymers. The transparency of the solid material employed for the device of the present invention, is desirably higher than 5%.

The first passage of the device of the present invention, has an inner tapered tube shape that inner diameter is reduced gradually from the both ends to middle section. Therefore, the inner diameters of both ends of the first passage are larger than those of the middle section of the first passage. Desirably, the inner diameters of both ends of the first passage is 10 μm to 200 μm and the inner diameters of middle section of the first passage is 3 μm to 150 μm.

The device of the present invention may comprise one or more of the second passage on which the material to be injected flows in order to put several materials into a cell at one try. The inner diameter of the second passage is desirably 10 nm to 1,000 nm.

The cells contained in the first passage of the present device may moves by pressure difference or by electric potential difference between the both ends of the first passage. The electric potential difference between the both ends of the first passage is desirably 10 V to 1,000 V, more desirably 15 V to 500 V, most desirably 20 V to 200 V.

Also, the electric potential difference between the first passage and the second passage is desirably 0.5 V to 100 V, more desirably 0.8 V to 50 V, most desirably 1.0 V to 10 V.

Another object of the present invention can be achieved by providing a process for forming a device for putting material into a cell within one solid material and comprises: the steps of: (i) forming a first passage on which the cell passes within the one solid by irradiation of LASER; (ii) forming a second passage on which the material passes and connected the second passage to the first passage at a position randomly selected between both ends of the first passage within the one solid by irradiation of LASER; and (iii) installing an apparatus which applies pressure difference or electric potential difference between the first passage and the second passage.

The LASER irradiated on a solid material in the present invention for forming the microchannels and nanochannels within the one solid material, may desirably be pulse laser, more desirably femto-laser of which pulse width is $10^{-15}$ second to $10^{-12}$ second.

The solid material employed for the present invention, is desirably a rigid material, such as, glass, thermoplastic polymers or thermosetting polymers, for example, polycarbonate, acrylics, epoxy resin or polyimide. The solid material of the present invention is desirably selected from thermoplastic polymers, thermosetting polymers or glass. The transparency of the solid material employed for the device of the present invention, is desirably higher than 5% for the laser beam machining.

The first passage of the device of the present invention is formed by the irradiation of the pulse laser into the inner tapered tube shape that inner diameter is reduced gradually from the both ends to middle section. Therefore, the inner diameters of both ends of the first passage are larger than those of the middle section of the first passage. Desirably, the inner diameters of both ends of the first passage is 10 μm to 200 μm and the inner diameters of middle section of the first passage is 3 μm to 150 μm.

The second passages which may be comprised one or more within the device of the present invention, are also formed within the solid by the irradiation of the pulse laser. The inner diameter of the second passage is desirably 10 nm to 1,000 nm.

The flow of the fluid containing the cell may effectively be controlled by adjusting the pressure difference or the electric potential difference applied on the first passage of the device of the present invention during watching the movement of the cells in the first passage through microscope.

In addition, the amount of the material to be injected into a cell may be controlled by adjusting the electric potential difference between the first passage and the second passage of the present invention. Also, the amount of the material injected into a cell may be calculated i) by measuring the intensity of the fluorescent conjugated on the material injected into a cell or ii) by the electric current measured upon injecting the material into a cell Hereinafter, the present invention will be described in greater detail with reference to the following examples and FIGS. However, the examples are given only for illustration of the present invention and not to be limiting the present invention within the following examples.

BRIEF DESCRIPTION OF FIGS.

Figure 1A:
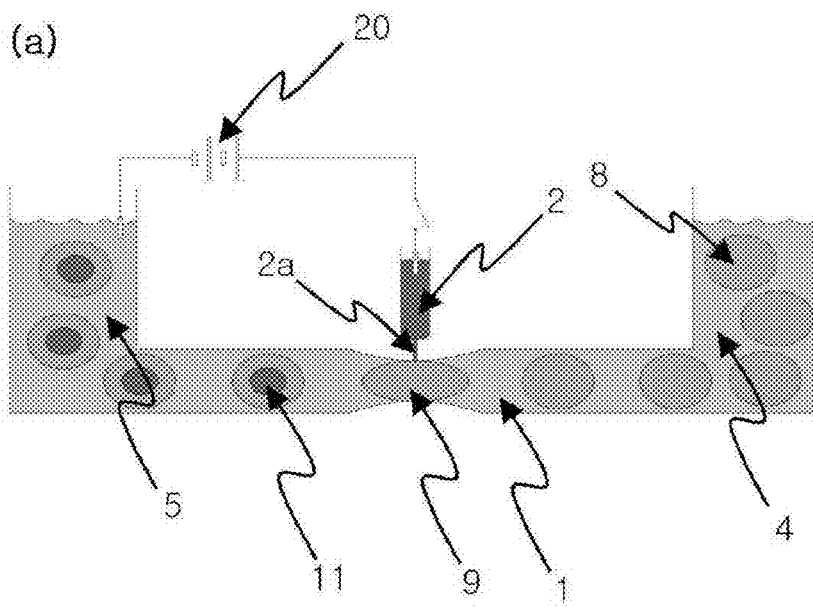
FIGS. 1a and 1b show schematic diagrams of the device of the present invention. Diagram a shows the device for injecting material into a cell which has one material passage (the second passage), and diagram b shows the device of the present invention which has three second passages.

Example 1: Process For Forming The Micro Channels And Nano Channels Of The Device Of The Present Invention Within One Solid Glass Femto-laser pulses (Pharos, 4 W, 190 fs, frequency doubled 510 nm, DPSS chirped pulse amplification laser system) had been focused on the single glass substrate through an objective lens (from 40× to 100×, N.A. from 0.5-1.3, Olympus & Zeizz), where the focus can move from the outside of the substrate into it. The glass substrate had been placed on the 3 axis linear nano-stage (100×100×100 μm3, ±1 nm, Mad City Labs, Inc., Madison, Wis.), by which the glass substrate had been able to be controlled in three-dimension against the focus with nanoscale accuracies.

As the focus of the femto-laser pulses had been controlled to move from the glass surface into it, the glass had been removed along the pathway of the focus. The pathways of the focus had been written as G-code to automatically machine true three-dimensional structures directly inside of the glass substrate. Thus, no glass-to-glass bonding had been required.

The entire process had been monitored by CCD camera. Although the minimum size of the femto-laser ablation of glass was found as 10 nm, the setup of the example had been designed to have feature size around 200 nm, and the feature size had been able to be controlled bigger or smaller than 200 nm by adjusting the optical parameters and components. Machining true three-dimensional structures had been possible by using transparent material like glass.

Example 2: Process Of Putting Red Fluorescence Protein Into Human Alveolar Basal Epithelial Cell By Using The Device Of The Present Invention RFP (dsRed fluorescence protein, MBS5303720) had been prepared by diluting to be 1 mg/ml (solvent: PBS, Hyclone, SH30028.02, pH 7.4). A549 cells (human alveolar basal epithelial cells) had been subcultured using 10% FBS DMEM (high glucose) in an incubator (humidified 5% $CO^2$, 37° C.).

The subcultured cells had been separated using TrypLE (gibco). And the solution had been replaced with the 1 mM EDTA in D-PBS (gibco) solution. Debris had been filtered using 40 μm cell strainer (BD), and then cells had been treated with Calcein-AM in an incubator (for 15 minutes, at 37° C.). After the solution had been replaced with 1 mM EDTA in D-PBS, A549 cell suspension solution of 2×10⁶ cells/ml concentration had been prepared using hemocytometer.

A549 cell suspension and RFP had been packaged in 1 ml syringes, and each of them had been connected with silicon tubes to the inlets of the cell loading and the material loading channels. And the other sides of the cell loading and the material loading channels had been connected with silicon tubes to the PBS filled 1 ml syringes.

By controlling all the syringes cells had been controlled to flow into the cell loading channels and each of them had been placed at the center of the cell loading channel where the material injection pathways were crossed.

Then, proper electric potentials had been applied to the both side of the material loading channel for 3 seconds to make the electric potential 1.76V along the material injection pathways. The electric potential had been measured by oscilloscope (VDS3102, Owon) and epifluorescent microscope (TE2000-U, 41-17Nikon) had been used to monitor cells and RFP injection process.

Example 3: Process For Putting Red Fluorescence Protein Into Human Umbilical Cord Tissue Mesenchymal Stem Cells By Using The Device Of The Present Invention RFP (dsRed fluorescence protein, MBS5303720) had been prepared by diluting to be 1 mg/ml (solvent: PBS, Hyclone, SH30028.02, pH 7.4). UC-MSCs (Human Umbilical Cord Tissue Mesenchymal Stem Cells) had been taken from the CHA hospital at Boondang South Korea. UC-MSCs had been subcultured using MEM-alpha (Gibco), 10% FBS (Hyclone), 25 ng/ml FGF-4 (Peprotech), 1 ug/ml Heparin (Sigma) in an incubator (humidified 5% $CO^2$, 37° C.).

The subcultured cells had been separated using TrypLE (gibco). And the solution had been replaced with the 1 mM EDTA in D-PBS (gibco) solution. Debris had been filtered using 40 μm cell strainer (BD), and then cells had been treated with Calcein-AM in an incubator (for 15 minutes, at 37° C.). After the solution had been replaced with 1 mM EDTA in D-PBS, UC-MSC suspension solution of 2×10⁶ cells/ml concentration had been prepared using hemocytometer.

UC-MSC suspension and RFP had been packaged in 1 ml syringes, and each of them had been connected with silicon tubes to the inlets of the cell loading and the material loading channels. And the other sides of the cell loading and the material loading channels had been connected with silicon tubes to the PBS filled 1 ml syringes.

By controlling all the syringes cells had been controlled to flow into the cell loading channels and each of them had been placed at the center of the cell loading channel where the material injection pathways were crossed.

Then, proper electric potentials had been applied to the both side of the material loading channel for 3 seconds to make the electric potential 1.4V along the material injection pathways. The electric potential had been measured by oscilloscope (VDS3102, Owon) and epifluorescent microscope (TE2000-U, 41-17 Nikon) had been used to monitor cells and RFP injection process.

Example 4: Process Of Putting Red Fluorescence Protein Into Human Placenta-Derived Mesenchymal Stem Cell By Using The Device Of The Present Invention RFP (dsRed fluorescence protein, MBS5303720) had been prepared by diluting to be 1mg/ml (solvent: PBS, Hyclone, SH30028.02, pH 7.4). PD-MSCs (Human Placenta-derived Mesenchymal Stem Cells) had been taken from the CHA hospital at Boondang South Korea. PD-MSCs had been subcultured using MEM-alpha (Gibco), 10% FBS (Hyclone), 25 ng/ml FGF-40 (Peprotech), 1 ug/ml Heparin (Sigma) in an incubator (humidified 5% $CO^2$, 37° C.).

The subcultured cells had been separated using TrypLE (gibco). And the solution had been replaced with the 1 mM EDTA in D-PBS (gibco) solution. Debris had been filtered using 40 μm cell strainer (BD), and then cells had been treated with Calcein-AM in an incubator (for 15 minutes, at 37° C.). After the solution had been replaced with 1 mM EDTA in D-PBS, PD-MSC suspension solution of $2 \times 10^6$ cells/ml concentration had been prepared using hemocytometer.

PD-MSC suspension and RFP had been packaged in 1 ml syringes, and each of them had been connected with silicon tubes to the inlets of the cell loading and the material loading channels. And the other sides of the cell loading and the material loading channels had been connected with silicon tubes to the PBS filled 1 ml syringes.

By controlling all the syringes cells had been controlled to flow into the cell loading channels, and each of them had been placed at the center of the cell loading channel where the material injection pathways were crossed.

Then, proper electric potentials had been applied to the both side of the material loading channel for 5 seconds to make the electric potential 0.8V along the material injection pathways. The electric potential had been measured by oscilloscope (VDS3102, Owon) and epifluorescent microscope (TE2000-U, 41-17 Nikon) had been used to monitor cells and RFP injection process.

Example 5: Process Of Putting Plasmid DNA(Cy3) Into Human Alveolar Basal Epithelial Cell By Using The Device Of The Present Invention Plasmid DNA(MIR7904, Mirus) had been prepared by diluting to be 10 μg/20 μl. A549 cells (human alveolar basal epithelial cells) had been subcultured using 10% FBS DMEM (high glucose) in an incubator (humidified 5% $CO^2$, 37° C.).

The subcultured cells had been separated using TrypLE (gibco). And the solution had been replaced with the 1 mM EDTA in D-PBS (gibco) solution. Debris had been filtered using 40 μm cell strainer (BD), and then cells had been treated with Calcein-AM in an incubator (for 15 minutes, at 37° C.). After the solution had been replaced with 1 mM EDTA in D-PBS, A549 cell suspension solution of $2 \times 10^6$ cells/ml concentration had been prepared using hemocytometer.

A549 cell suspension and RFP had been packaged in 1 ml syringes, and each of them had been connected with silicon tubes to the inlets of the cell loading and the material loading channels. And the other sides of the cell loading and the material loading channels had been connected with silicon tubes to the PBS filled 1 ml syringes.

By controlling all the syringes cells had been controlled to flow into the cell loading channels, and each of them had been placed at the center of the cell loading channel where the material injection pathways were crossed.

Then, proper electric potentials had been applied to the both side of the material loading channel for 2 seconds to make the electric potential 1.0V along the material injection pathways. The electric potential had been measured by oscilloscope (VDS3102, Owon) and epifluorescent microscope (TE2000-U, 41-17Nikon) had been used to monitor cells and RFP injection process.

After the injection of Plasmid DNA into A549 cells, the harvested cells had been distributed in the 96 well plate with 200 μl culture fluids. After culturing for 12 hours (humidified 5% $CO^2$, 37° C.), red fluorescence inside of the cells had been induced to confirm that the plasmid DNA had been successfully expressed.

Figure 1B:
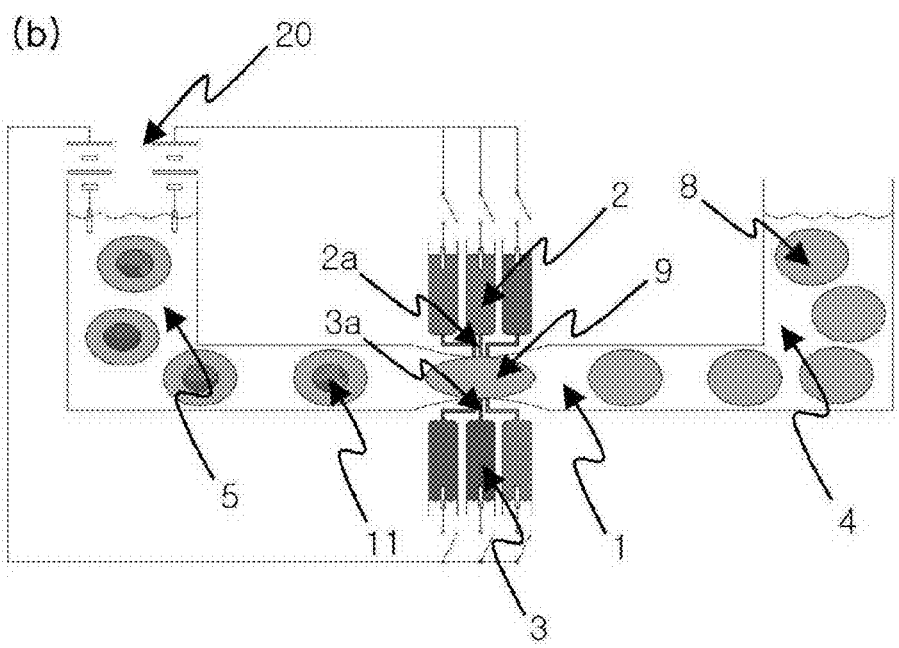

For reference to FIG. 1, the device of the present invention has one material passage (the second passage, image a) or has three second passages (the second passage, image b) are shown.

In the FIG. 1, the cell (8) to be injected with the material, moves through the first passage. The electrical potential difference occurs between the second passage (2) which injects the material and the first passage by the external power (20). The material (2a) is injected to the cell (9) by the electrical potential difference between the cell and the second passage when the cell (8) passes the narrowed middle section of the first passage. The cell which has been injected with material (11) is moved to the cell draw off passage (5) one after another.

In image b of FIG. 1, the device of the present invention injecting six (6) materials by employing the six (6) second passage is represented. Using the device illustrated in image b of FIG. 1, it is possible to put six materials into a cell at a time.

In FIG. 1, it is possible to control the amount of each material to be put into an individual cell by adjusting the electrical potential difference between the first passage and the each second passage.

Figure 2:
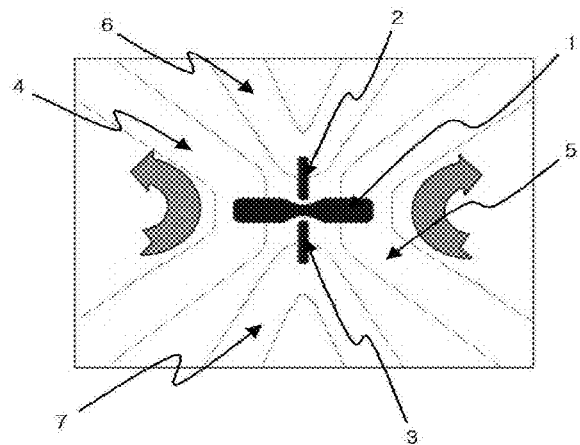
FIG. 2 is a schematic diagram of the device of the present invention.

In the FIG. 2, there are the outflow and inflow channels (4) of the solution containing the cell, the outflow (7) and inflow (6) channels of material, the passage (1) and channel (5) which take back the cell that has been injected with material, the first passage (1) which has a shape of narrowed middle section, and the two second passages (2,3) which is connected to the middle section of the first passage (1).

During the cell passes through the narrowed portion of the middle section of the first passage (1), the cell is inserted and held on the inner wall of the middle section of the first passage. By this close contact between the cell and the wall of the middle section of the first passage (1), the drop of the electrical potential difference between the first passage (1) and second passage (2, 3) is minimized. The cell that has been injected with the material can easily be moved to the widened portion of the other side of the first passage.

The second passage (2, 3) plays a role as like an injection needle. That is, the charge focused on the second passage (2a, 3a) by an external electrical power provides the function of boring the cell membrane (or cell wall) of the individual cell which is closely contacted to the second passage (2a, 3a), and the driving force for injecting the material into the cell through the pore formed by the boring.

By applying pressure difference (for example by using a pump) or by applying electrical potential difference (for example by using external electrical potential with direct current or alternating current) to the inflow and outflow channels (FIGS. 2, 4) of solution containing the cells (8 of FIG. 1, images a and b), the cell moves through the first passage (1). After the injection of material into the cell, the cell moves to the other side of the first passage (5 of FIG. 1, images a and b).

The inflow and outflow channels (6, 7 of FIG. 2) for material to be injected, intake and discharge the material by pressure difference or electrical potential difference between the inflow channel and outflow channel. Also, during the individual cell is closely contacting with the second passage in the narrowed middle section of the first passage, micro pore is generated on the cell membrane (or cell wall) and then the material is injected into the cell by the electric potential difference.

Figures 3A, 3B:
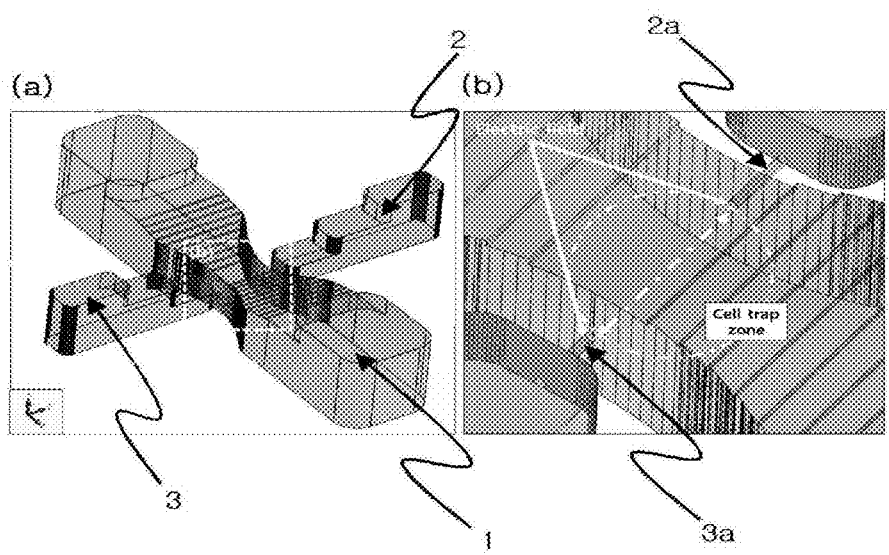
FIGS. 3a and 3b shows a three dimensional structure of the first passage and the second passage of the device of present invention for injecting material into a cell (image a), and image b is an enlarged diagram for the part which connects the first passage and the second passage.

As represented in FIG. 3, the second passages (2,3) are connected to the narrowed middle section of the first passage (1).

Figure 4:
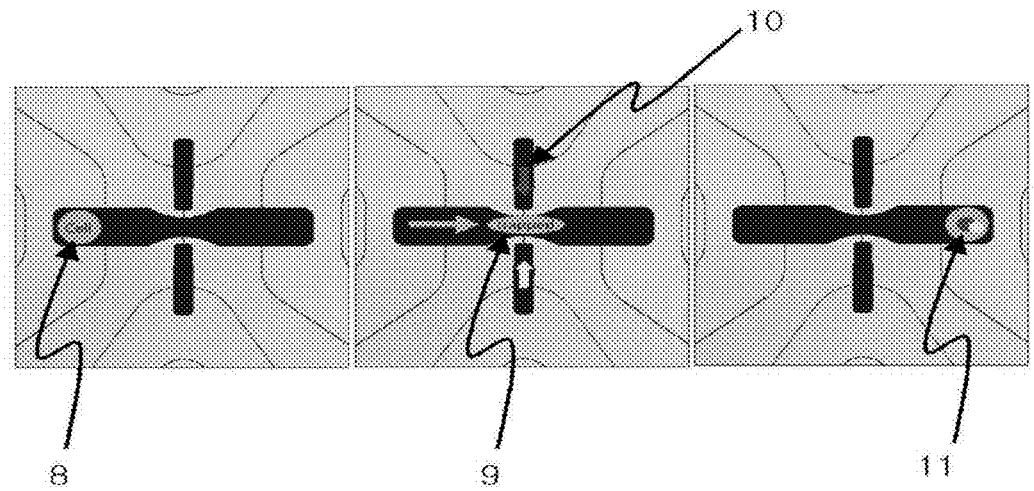
FIG. 4 is a schematic diagram which shows the process for injecting material into a cell, in Examples 2 to 5 of the present invention.

The FIG. 4 illustrates a process of injecting two kinds of materials into a single cell. The two materials are injected (11) into the cell trapped in the narrowed middle section of the first passage (9) through which the second passages (10) are connected, and then the cell injected with the material is retrieved through the outflow channel connected to the first passage.

Figure 5:
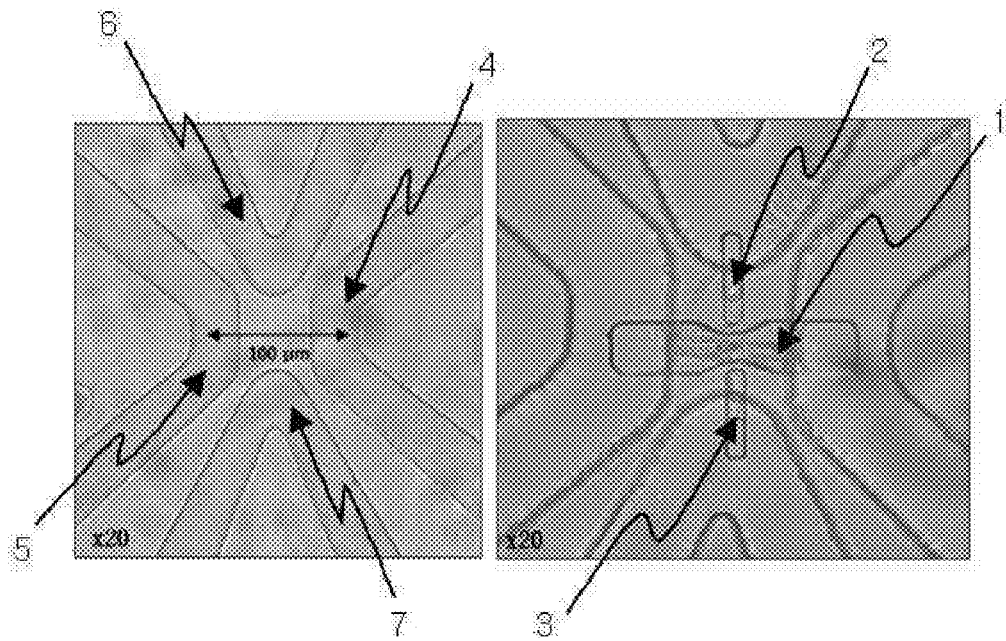
FIG. 5 is the microscopic images for the device of the present invention for injecting material into a cell, prepared in Example 1 of the present invention.

The left microscopic image of FIG. 5 shows the inflow and outflow channel (5) of solution containing the cell, the inflow and outflow channels (6, 7) of material which will be injected into the cell, and the outflow channel (4) of retrieving the cell into which the material has been injected.

In addition to the left image in FIG. 5, the right image of FIG. 5 shows the first passage (1) having the narrowed middle section and connected at the both of ends to the inflow and outflow channel (5) and the channel (4) of retrieving the cell into which the material has been injected. The microscopic images of FIG. 5 also show the two second passage (2, 3) formed within the glass and connected to the narrowed middle section of the first passage.

Figure 6:
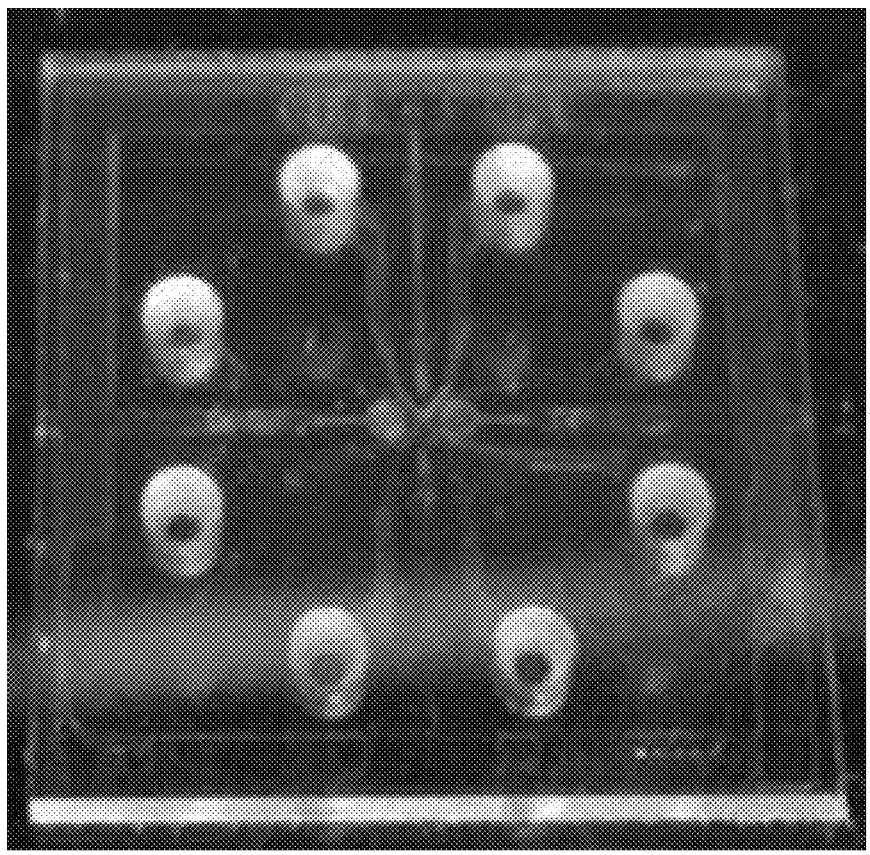
FIG. 6 is a photograph of external appearance of the device of the present invention for putting material into a cell.

FIG. 6 is a photograph of external appearance of the device of the present invention for putting material into a cell.

Figures 7A, 7B, 7C, 7D, 7E, 7F:
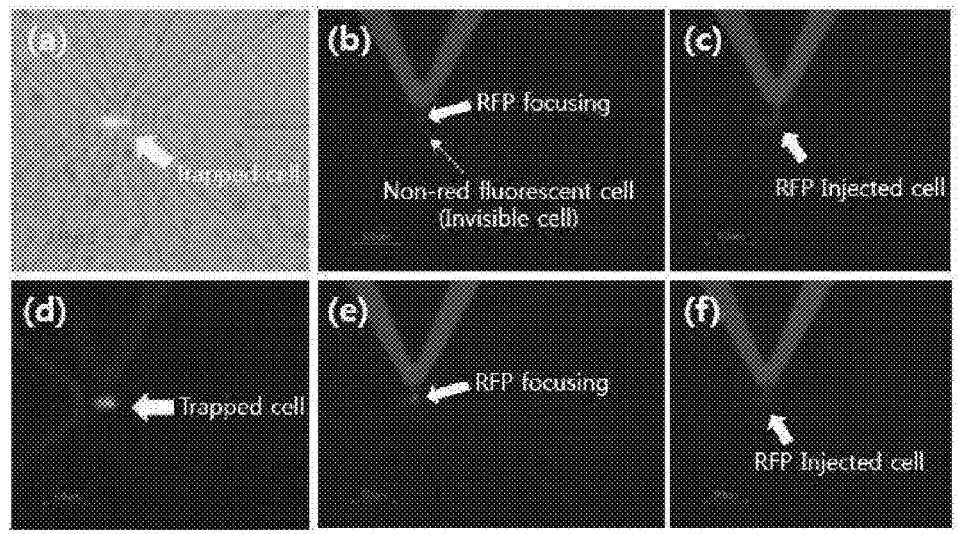
FIGS. 7a, 7b, 7c, 7d, 7e and 7f shows the microscopic images (a-f) showing the process of injecting the red fluorescent protein into the human alveolar basal epithelial cell A549 in Example 2 of the present invention.

FIG. 7 shows the photographs of fluorescence microscope of the proceedings of injecting the red fluorescence protein (RFP) into the human alveolar basal epithelial cell A549 in Example 2. The aliveness of the human alveolar basal epithelial cell after injection with the red fluorescence protein, was confirmed by means of the test of ascertaining green fluorescence from the human alveolar basal epithelial cell treated with Calcein AM (fluorescent dye).

Image a of FIG. 7 shows that the live (green fluorescence) A549 cell locates in the middle section of the first passage. Image b of FIG. 7 shows that when the electrical potential difference is applied between the first passage and the second passage, RFP which has been moved along the second passage, starts to be injected into the A549 cell (red fluorescent). Image c of FIG. 7 shows the fact that RFP is being injected into the A549 cell (red fluorescent) certainly. Image d of FIG. 7 shows that the A549 cell (green fluorescent) is alive after the RFP injection. Images e and f of FIG. 7 show that RFP has been injected successfully into the A549 cell after the repeating two times the above procedure.

Figures 8A, 8B, 8C, 8D, 8E, 8F:
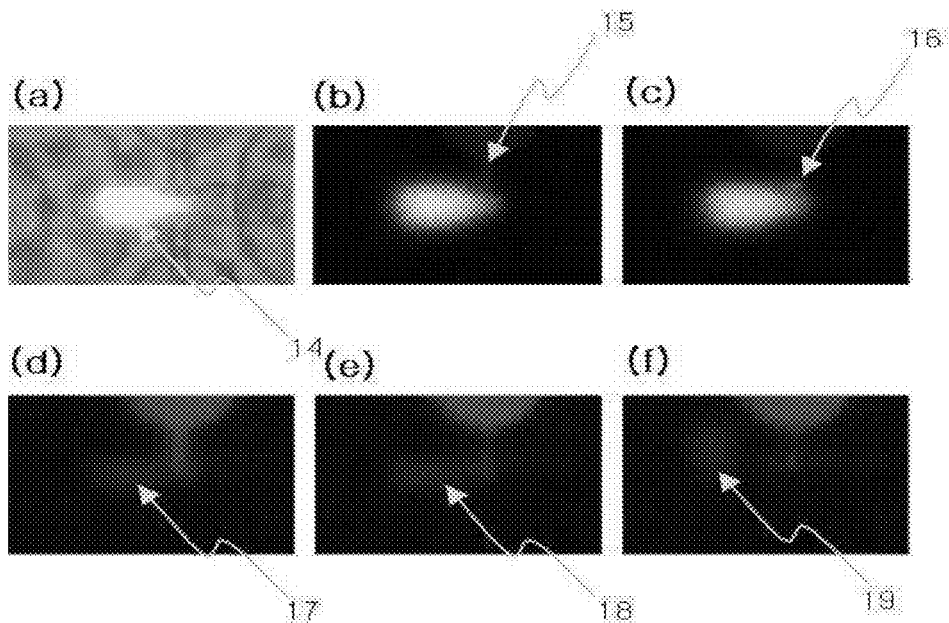
FIGS. 8a, 8b, 8c, 8d, 8e and 8f shows the photographs (a-f) magnifying the cell part in the process of injecting the red fluorescent protein into the human umbilical cord stem cell in Example 3 of the present invention.

FIG. 8 shows the photographs of fluorescence microscope of the proceedings for injecting RFP into the human umbilical cord stem cells. As described in the above explanation of FIG. 7, the aliveness of the human umbilical stem cell was confirmed by using the Calcein AM.

Photograph a of FIG. 8 shows that the human umbilical cord stem cell located in the middle section of the first passage is alive by means of the green fluorescence (14). Photograph b of FIG. 8 shows that the second passage is stocked with RFP by means of the red fluorescence (15), and that injection of RFP into the human umbilical cord stem cell is prepared well by means of the green fluorescence. Photograph c of FIG. 8 shows that the injection of RFP is starting upon the application of the electrical field on the passages by means of the appearance of the brighter red fluorescence (16). Photograph d of FIG. 8 shows that the umbilical cord stem cell is moving to the exit side of the first passage by means of the red fluorescence (17). Photograph f of FIG. 8 shows that umbilical cord stem cell is totally discharged from the first passage by means of the red fluorescence (19).

Figures 9A, 9B, 9C, 9D:
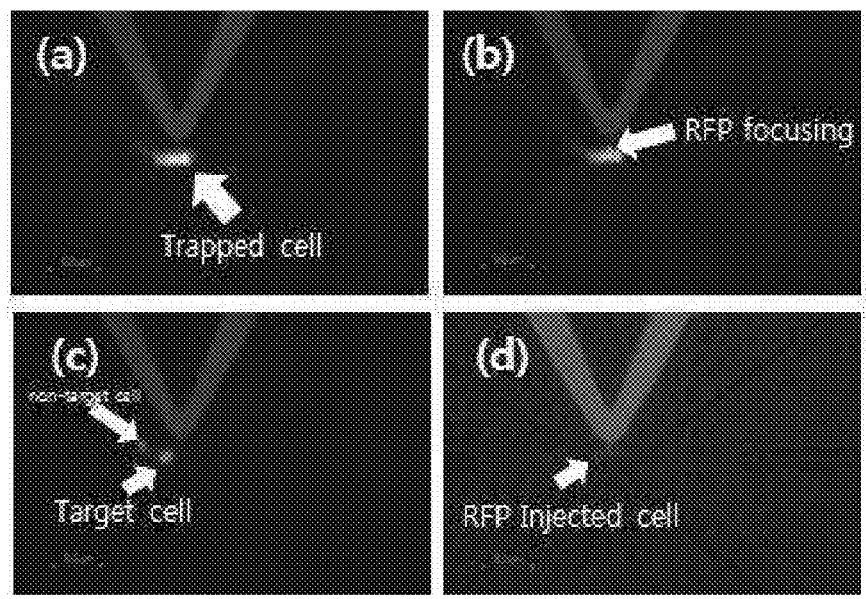
FIGS. 9a, 9b, 9c and 9d show the photographs (a-d) of fluorescence microscope of the proceedings of injecting RFP into the human placental stem cell in Example 4 of the present invention.

FIG. 9 shows the photographs of fluorescence microscope of the proceedings of injecting RFP into the human placental stem cell. As described in the above explanation of FIG. 7, the aliveness of the human umbilical stem cell was confirmed by using the Calcein AM.

Figures 10A, 10B, 10C, 10D:
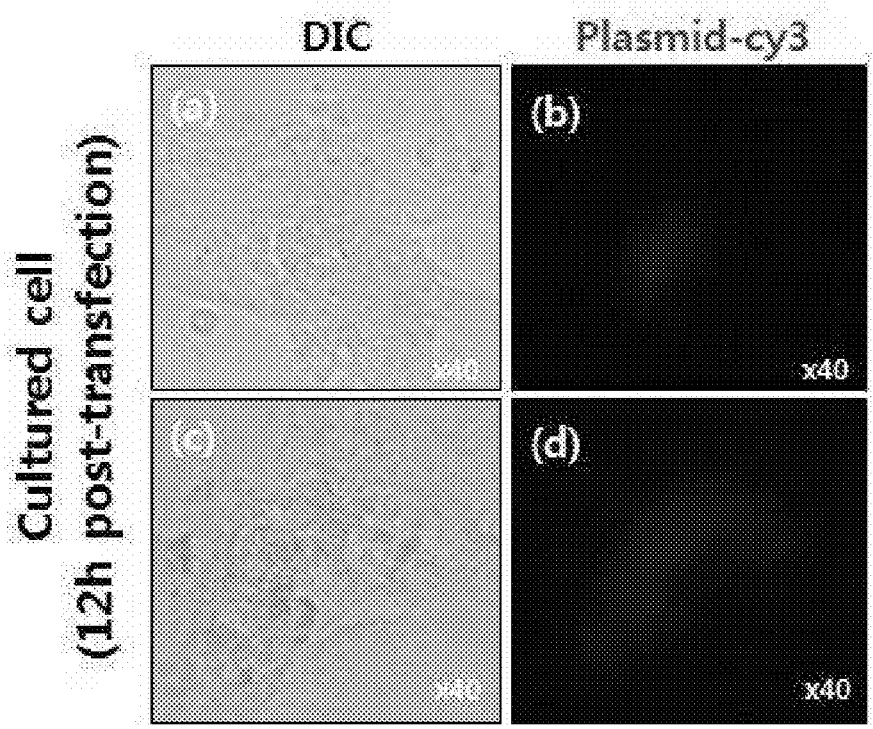
FIGS. 10a, 10b, 10c, 10d show the images (a-d) of human alveolar basal epithelial cell A549, after the lapse of 12 hours from the injection of plasmid DNA(cy3) in Example 5 of the present invention.

FIG. 10 shows the images of human alveolar basal epithelial cell A549 after the lapse of 12 hours from the injection of plasmid DNA (cy3) described in Example 5.

Figure 11:
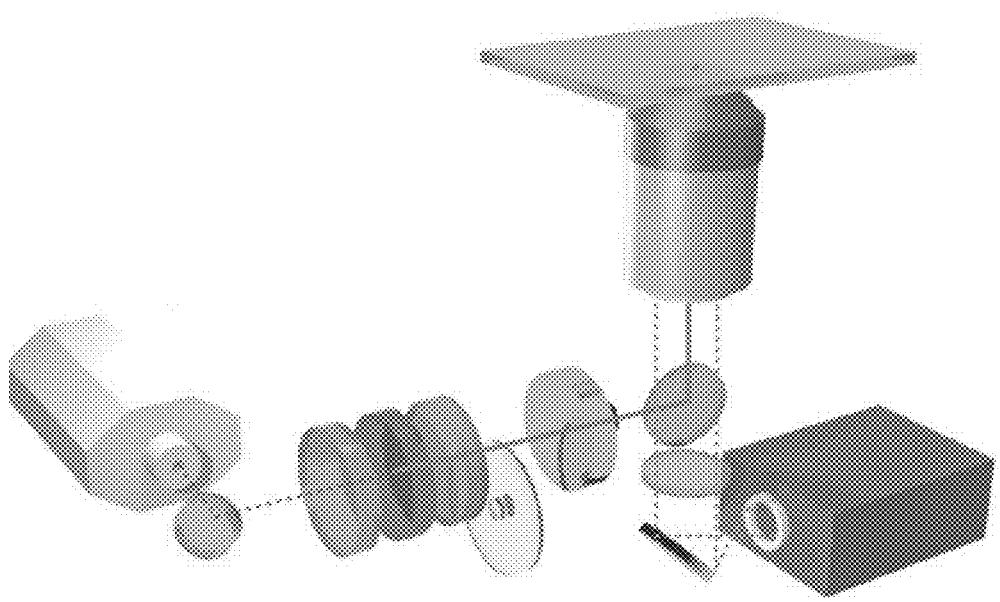
FIG. 11 shows a disassembled perspective view of the laser beam machine employed for the processing of the device of the present invention, according to Example 1.

FIG. 11 shows a disassembled perspective view of the laser beam machine employed for the processing of the device of the present invention, described in Example 1.

Advantageous Effects

As explained above, through the device of the present invention, various materials such as protein, gene, plasmid, drug, nanoparticle can be putting into live-cell. Particularly, the amount of the material put into a single cell can be controlled by adjusting the electrical potential difference. The amount of the material injected into each live-cell can be controlled quantitatively. Therefore, it is possible for the present invention to be applied for a great variety of cell manipulation and development of cellular therapeutics including IPS stem cells.

The foregoing examples 1 to 5 and the description of FIGS. 1 to 11 for the preferred embodiments should be taken as illustrating, rather than as limiting the present invention as defined by the claims.

As will be readily appreciated by a person skilled in the art, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:
1. A system comprising:
a device formed within one solid material for introducing a substance into a cell, the one solid material being selected from a glass, a thermoplastic polymer, or a thermosetting polymer, the device comprising:
an inflow channel having a first middle section;
an outflow channel having a second middle section;
a first passage on which the cell passes having two ends and a third middle section in between the two ends, wherein one end of the two ends is connected to the first middle section of the inflow channel and the other end is connected to the second middle section of the outflow channel; and
a second passage on which the substance passes, the second passage being connected to the third middle section of the first passage; and
an apparatus which applies a pressure difference or an electric potential difference on the first passage and the second passage of the device,
wherein the device is formed without bonding.
2. The system according to claim 1, wherein the device comprises one or more of the second passage.
3. The system according to claim 1, wherein each of the two ends of the first passage has a diameter larger than a diameter of the third middle section of the first passage.

4. The system according to claim 3, wherein an inner diameter of the two ends of first passage is 10 µm to 200 µm.

5. The system according to claim 3, wherein an inner diameter of the third middle section of the first passage is 3 µm to 150 µm.

6. The system according to claim 1, wherein an inner diameter of the second passage is 10 nm to 1,000 nm.

7. The system according to claim 1, wherein the cell moves by pressure difference or electric potential difference between the two ends of the first passage.

8. The system according to claim 7, wherein the electric potential difference between the first passage and the second passage is 0.5 V to 100 V.

9. The system according to claim 8, wherein the electric potential difference between the first passage and the second passage is 0.8 V to 50 V.

10. The system according to claim 9, wherein the electric potential difference between the first passage and the second passage is 1.0 V to 10 V.

11. The system according to claim 1, wherein a transparency of the one solid material is higher than 5%.

12. The system according to claim 1, wherein the one solid material is a glass.

\* \* \* \* \*